(12) United States Patent
Josimovic-Alasevic et al.

(10) Patent No.: US 6,713,269 B2
(45) Date of Patent: *Mar. 30, 2004

(54) METHODS FOR IDENTIFYING POTENTIAL THERAPEUTIC AGENTS FOR TREATMENT OF OSTEOPOROSIS USING MITOGENIC INDICES

(75) Inventors: Olivera Josimovic-Alasevic, Berlin (DE); Karl-Gerd Fritsch, Berlin (DE); Jochen Ittner, Augsburg (DE)

(73) Assignee: co.don Aktiengesellschaft, Teltow (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/973,116

(22) PCT Filed: Jun. 7, 1996

(86) PCT No.: PCT/DE96/01042
§ 371 (c)(1),
(2), (4) Date: Mar. 27, 1998

(87) PCT Pub. No.: WO96/40873
PCT Pub. Date: Dec. 19, 1996

(65) Prior Publication Data
US 2002/0076730 A1 Jun. 20, 2002

(30) Foreign Application Priority Data
Jun. 7, 1995 (DE) .......................................... 195 21 942
Jan. 5, 1996 (DE) .......................................... 196 01 052

(51) Int. Cl.$^7$ .......................................... G01N 33/567
(52) U.S. Cl. .......................... 435/7.21; 435/4; 435/325
(58) Field of Search .......................... 435/4, 6, 7.1, 7.2, 435/7.21, 325, 366, 372, 375; 424/9.1, 9.2

(56) References Cited

FOREIGN PATENT DOCUMENTS

EP 0585801 3/1994

OTHER PUBLICATIONS

Manduca, P., et al., 1993, "Differential expression of alkaline phosphatase in clones of human osteoblast–like cells", J. Bone Mineral Res. 8(3):291–300.*

Ingram, R. T., et al., 1994, "Effects of transforming growth factor beta (TGFβ) and 1,25 dihydroxyvitamin $D_3$ on the function, cytochemistry, and morphology of normal human osteoblast–like cells", Different. 55:153–163.*

Lind, M., et al., 1995, "Chemotaxis of human osteoblasts", APMIS 103:140–146.*

Marie, P. J., et al., 1989, "Osteocalcin and deoxyribonucleic acid synthesis in vitro and histomorphometric indices of bone formation in postmenopausal osteoporosis", J. Clin. Endocrin. Metab. 69(2):272–278.*

Breen, E. C., et al., 1994, "TGFβ alters growth and differentiation related gene expression in proliferating osteoblasts in vitro, preventing development of the mature bone phenotype", J. Cell. Physiol. 160:323–335.*

M. Kassem et al., European Journal of Endocrinology, 130:381–386 (1994).

M. M. Wong, Osteoporosis International, 4:21–31 (1994).

P. J. Marie, Journal of Clinical Investigation, 88:1167–1172 (1991).

L. Risteli, Annals of Medicine, 25:385–393 (1993).

M. Kassem, Calcified Tissue International, 54:1–6 (1994).

P. J. Marie, Journal of Clinical Endocrinology and Metabolism, 77(1):824–829 (1993).

BIOSIS: 91:292164.

BIOSIS: 89:331475.

Chemical Abstract, vol. 119, 1993, Ref. 268655K.

Chemical Abstract, vol. 102, 1985, Ref. 125570S.

* cited by examiner

Primary Examiner—Laurie Scheiner
Assistant Examiner—Jeffrey S. Parkin
(74) Attorney, Agent, or Firm—Birch, Stewart, Kolasch & Birch, LLP

(57) ABSTRACT

A method of screening potential therapeutic substances that may be useful in the treatment of osteoporosis is provided herein utilizing primary osteoblast precursor cell cultures to determine the mitogenic effect of the tested agents. This method comprises preparation of the primary cultures from osteoporotic patients for the expression of several intracellular proteins in early and late osteoblast differentiation phases, expression of other proteins involved in matrix synthesis, and quantitative analysis of the cellular proliferation rate. The expression of such intracellular proteins and cell proliferation in the cultures derived from osteoporotic patients are quantitatively compared to primary osteoblast cell cultures from non-osteoporotic patients that are standardized for the same approximate age and sex.

3 Claims, 6 Drawing Sheets

METHODS FOR IDENTIFYING POTENTIAL THERAPEUTIC AGENTS FOR TREATMENT OF OSTEOPOROSIS USING MITOGENIC INDICES

This application claims the benefit under 35 U.S.C. §371 of prior PCT International Application No. PCT/DE96/01042 which has an International filing date of Jun. 7, 1996 which designated the United States of America, the entire contents of which are hereby incorporated by reference.

FIELD OF THE INVENTION

The invention relates to standardized, primary osteoblast cell cultures from test persons with suspected osteoporosis, examined using differential diagnosis, their use in osteoporosis diagnostics, and in testing potential therapeutic agents for osteoporosis, and a method for diagnosing osteoporosis permitting a 95% reliable statement as to the presence of osteoporosis, and a method for testing potential osteoporosis therapeutic agents, by which an effective osteoporosis therapeutic agent can be determined for each individual case.

BACKGROUND OF THE INVENTION

Osteoporosis (bone atrophy) is a severe systemic disease of the skeleton, which is characterized by a reduced bone density (mass) occurring with a mosaic-like pattern and micro-structural changes in the bone tissue. The bone tissue of a healthy adult person is subject to continuous formation and degradation even after completed development. Normally, two opposing processes are balanced. In the event of a prevailing degradation phase (bone resorption), however, the initial result will be bone atrophy (osteoporosis), i.e., reduced bone stability. The disease is accompanied by mostly lifelong pain, more frequent fractures, which may be followed by complications up to a fatal course. It is estimated that more than 200 million people worldwide, 7–8 millions in Germany, suffer from the above disease.

Therapeutic agents currently used against osteoporosis, such as estrogens, progesterones, calcitonin, di/bisphosphonates and calcium are merely capable of slowing down or reducing bone atrophy as a result of their effectiveness as anti-bone resorbers. Using the above, there is no success in replacing bone substance which has already been lost.

The effects of the following factors on bone growth are currently investigated: Parathyroid hormone (PTH) and derivatives thereof, vitamin D3, anabolic steroids, fluorides, insulin-like growth factors I and II, prostaglandins and growth hormone (GH). The results of clinical studies published up to now are far from sufficient because the increase in bone density with most factors is only 1–3% per 1–3 years (clinical symptoms of osteoporosis frequently appear only after 50% of the bone mass has been lost) and frequently, the fracture rates are not reduced. Thus, in order to be capable of counteracting massive progress of this disease, early recognition of osteoporosis and generally, diagnosis of osteoporosis play an important role.

Currently used physical diagnostic methods such as single photon absorptiometry (SPA), single and dual X-ray absorptiometry (SXA; DXA) and quantitative computed tomography (QCT) are costly; they are available at major clinical centers only and extremely difficult to interpret. Ultrasound examinations and X-ray photodensitometry are low-cost methods but involve similar drawbacks.

The currently used classical biochemical methods for diagnosing osteoporosis are based on the determination of hydroxyproline in urine, calcium excretion, alkaline phosphatase and osteocalcin in serum. The determination of these parameters in serum is non-specific because the values measured are highly variable.

New methods for estimating the bone resorption, such as the measurement of deoxypyridinoline in urine, or methods for determining the bone formation, such as the measurement of bone-specific alkaline phosphatase and procollagen peptides in serum should provide more information.

However, all the above-mentioned methods are disadvantageous in that they provide indications not before part of the bone mass has already been lost.

SUMMARY OF THE INVENTION

It was therefore the object of the invention to provide a low-cost method for diagnosing osteoporosis, which is easy to handle for a person skilled in the art and provides in each individual case an at least 95% reliable classification into groups of persons suffering from osteoporosis and those not suffering from osteoporosis or with respect to therapeutic success by unequivocally interpretable and reproducible parameters.

The object of the invention is accomplished in that for the first time, standardized osteoblast cell cultures from osteoporotic patients are established according to claim 1, which are viable for months and excellently useful in diagnosing osteoporosis.

It was found that osteoblast cells according to the invention obtained from osteoporotic patients exhibit pathological changes in their proliferation and differentiation when compared to osteoblast cells from non-osteoporotic patients. Using discriminant analysis, the data concerning proliferation rate and expression intensity of osteoblast-specific differentiation markers are assigned to osteoporotic and non-osteoporotic patients with an accuracy of more than 95%, where persons suffering from osteoporosis and those not suffering from osteoporosis exhibit highly significant differences.

Surprisingly, these cell cultures are also excellently suited for testing potential osteoporosis therapeutic agents, thereby permitting an individually effective therapeutic agent to be determined for each patient.

Arrows: Intensity differences of six proteins compared to FIG. 2.

Figure 2:
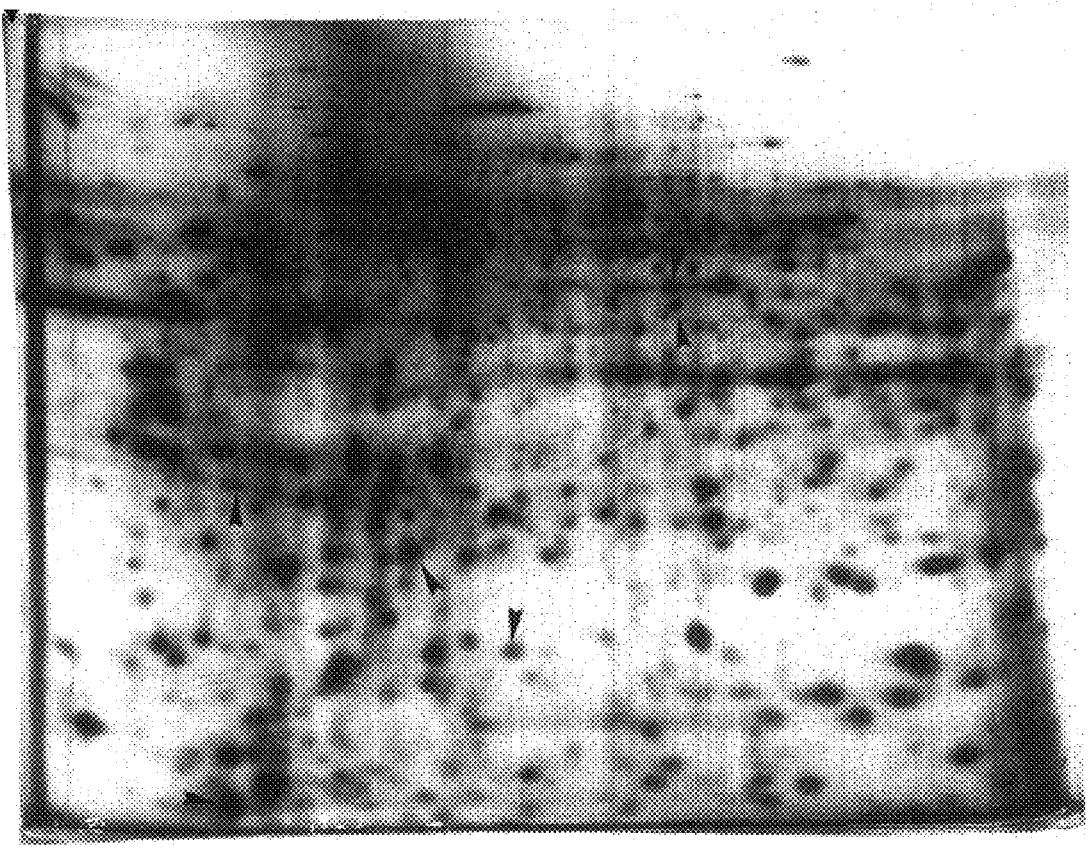

FIG. 2. High-resolution 2D SDS PAGE gel with the standardized primary osteoblast cell cultures from non-osteoporotic patients, showing the expression pattern of intracellular proteins according to spot distribution.

Arrows: Intensity differences of six proteins compared to FIG. 1.

Figure 3:
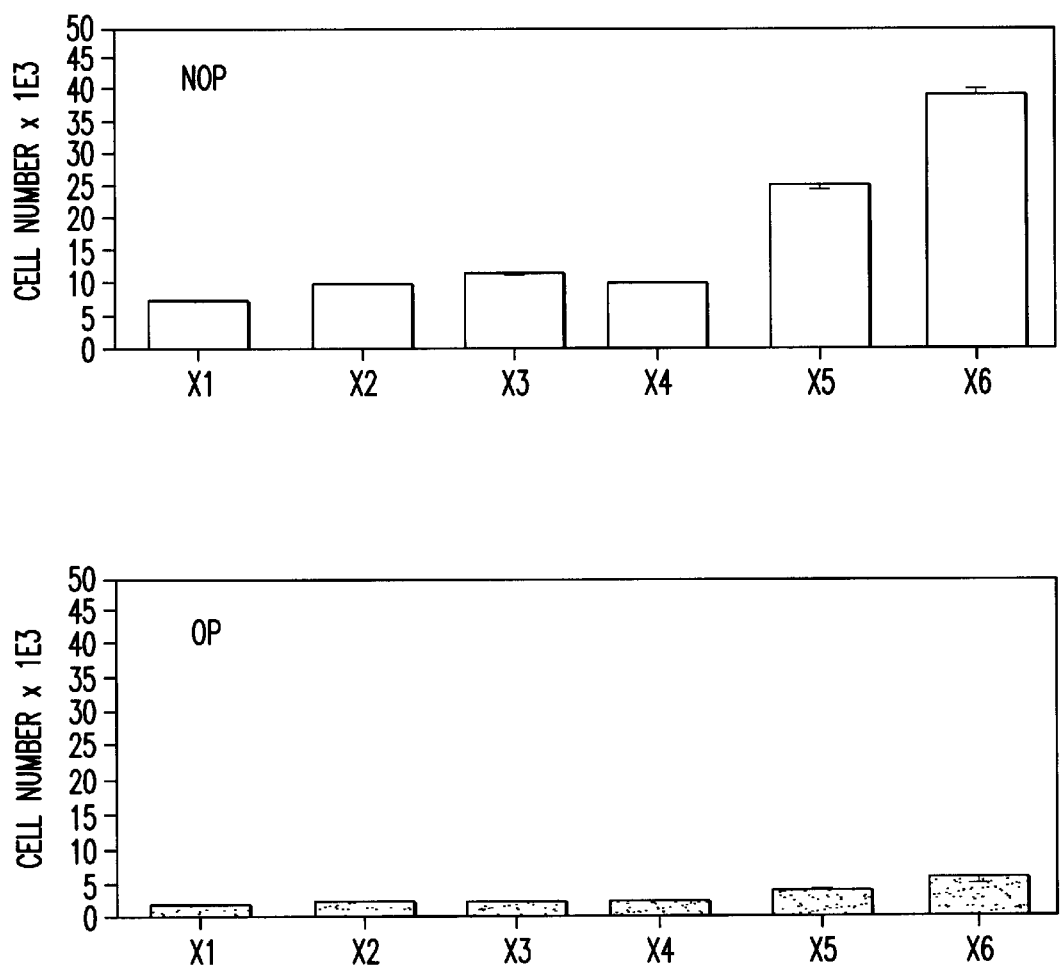

FIG. 3. Detection of reduced proliferation rate of osteoblast precursor cells from osteoporotic patients (OP cells) compared to the proliferation rate of osteoblast precursor cells from non-osteoporotic patients (NOP cells)

x1–x3: Treatment using FCS (fetal calf serum) 48 h, 120 h, 192 h x4–x6: Treatment using inactivated human control serum, 48 h, 120 h, 192 h (cf., Embodiment 3)

Figure 4:
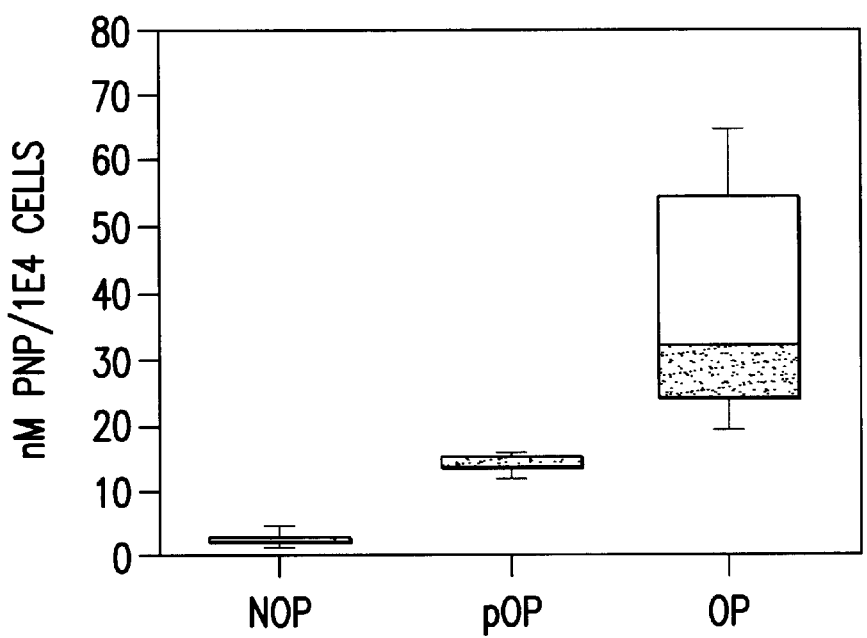
Figure 5:
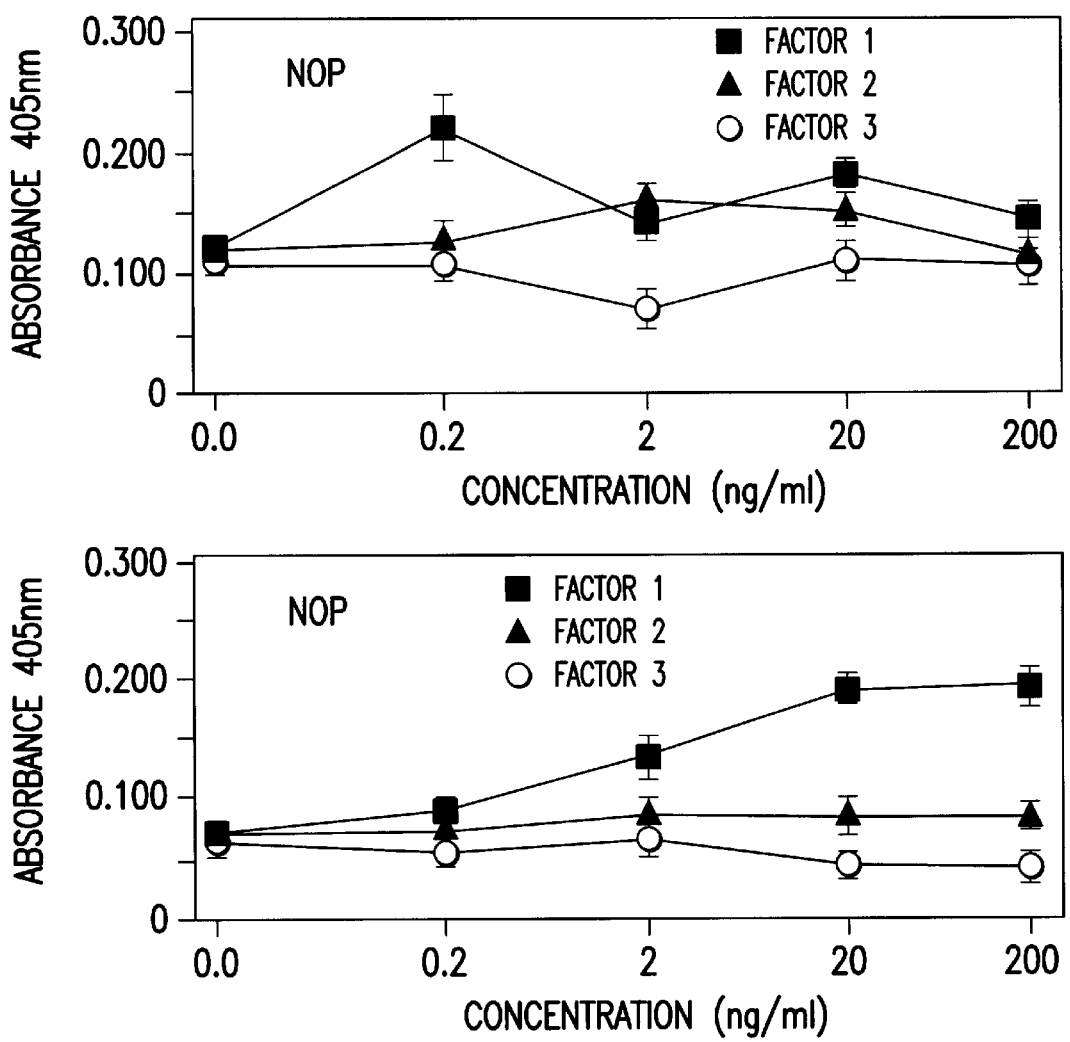

FIG. 4. Detection of increased expression of intracellular alkaline phosphatase in osteoblast precursor cells from osteoporotic patients (pOP and OP cells)

pOP: preclinical osteoporosis, n =12
OP: osteoblast, n =14
NOP: non-osteoporotic, n =18
10% FCS, 192 h FIG. 5: Various dose-effect curves (stimulative capability) of NOP and OP cell proliferation by proteins (growth factors 1, 2, and 3). A significant dose-dependent mitogenic effect of growth factor 1 (TGF-$\beta_2$) on osteoblast cells from osteoporosis patients is apparent.

Figure 6:
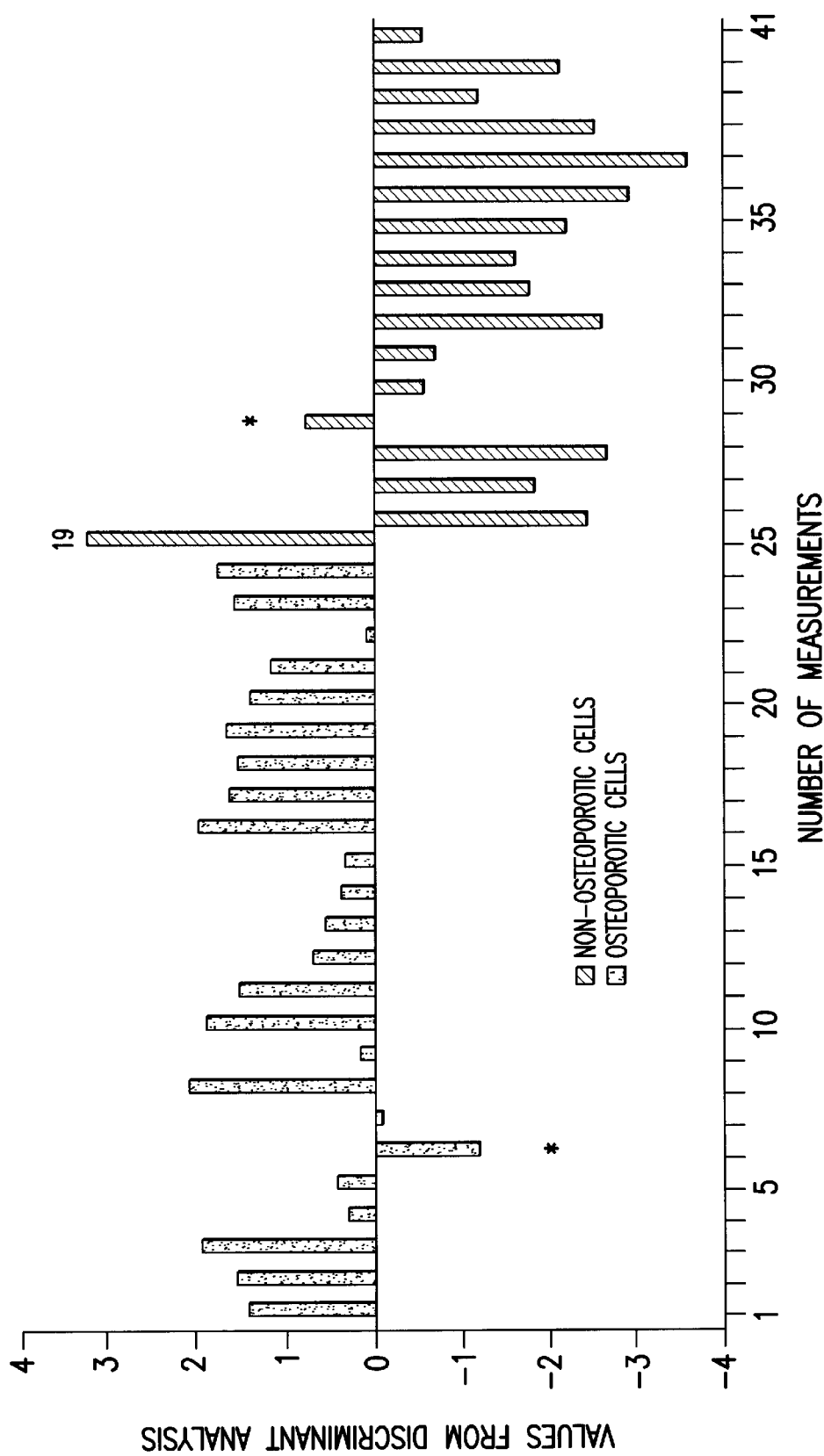

FIG. 6. Discriminant analysis (25 samples) of osteoblast cells from patients suffering from osteoporosis (OP) and those not suffering from osteoporosis (NOP).

The bone cell cultures are prepared by recovering osteoblast precursor cells from transiliacal bone biopsies from osteoporotic test persons by sequential enzymatic digestion, cultivating and establishing these cells as standardized cell cultures (equal cell population). The osteological bone biopsies are taken from clinically characterized patients, preferably from the iliac crest or from other bones as well (bone punching). The bone biopsies about 1–2 cm in length and 1–5 mm in thickness are separated mechanically from fat and connective tissues possibly present, divided into several pieces, treated enzymatically (preferably using collagenase) for several times, and the isolated osteoblast precursor cells are cultivated as a monolayer. In parallel, three-dimensional cell cultures may be established on denatured collagen type 1 pads, from which standardized bone cell cultures are produced. Primary bone cells recovered from non-osteoporotic patients of same sex and about same age serve as control.

The cell culture medium preferably consists of $\alpha$-MEM medium and HAM-F12 medium (Gibco) and optionally includes added serum. The ratio of $\alpha$-MEM medium and HAM-F12 medium is preferably 1:2; otherwise, ratios between 3:1 to 1:3 also furnish the desired result. Fetal calf serum, human serum, bovine serum albumin or Ultroser serve as serum additive which may range between 1–12%. It is preferred to use 2–7% of Ultroser, more preferably 2–5% of Ultroser.

According to the invention, by selecting the above described cell culture conditions, success has been achieved in maintaining viability of the standardized osteoblast cell cultures from osteoporotic patients over months and up to 2 years, the diagnostic method of the invention being performed using cell cultures up to the 2nd passage, because they represent the best reflection of the situation in the human body.

The cell extracts recovered from primary osteoblast cell cultures according to the invention were examined using high-resolution 2D gel electrophoresis and silver staining and compared to cell extracts recovered from osteoblast cell cultures from non-osteoporotic patients.

Figure 1:
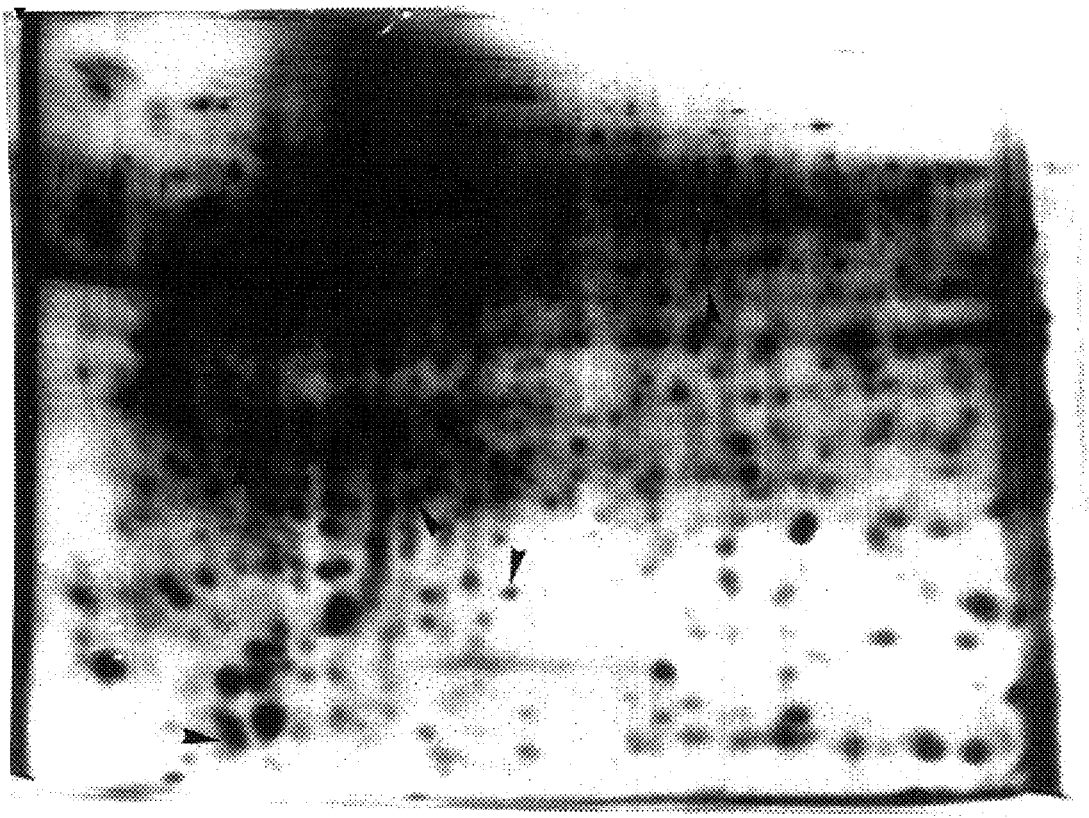
FIG. 1. High-resolution 2D SDS PAGE gel with standardized primary osteoblast cell cultures from osteoporotic patients, showing the expression pattern of intracellular proteins according to spot distribution.

It was found that cell cultures according to the invention obtained from osteoporotic patients exhibit a typical, reproducible expression pattern of about 700 intracellular proteins in the high-resolution 2D SDS PAGE gel according to the spot distribution in FIG. 1.

This protein expression pattern is identical with the protein expression pattern of osteoblast cell cultures from non-osteoporotic patients (cf., FIG. 2). When comparing the intensities of the individual spots in FIG. 1 and FIG. 2, however, reproducible and quantitatively measurable differences in at least six spots were apparent (cf., arrow marks in FIG. 1 and FIG. 2), where reduced expression of five proteins and an increased expression of one protein in the osteoblast cell cultures according to the invention as compared to osteoblast cell cultures from non-osteoporotic patients could be observed. Thus, using the spot intensities, a complementary statement concerning the presence of osteoporosis can be made.

The osteoblast cell culture protein expression patterns obtained according to the invention were also compared to those of human fibrosarcomas and human osteosarcomas. It appeared that the protein expression patterns of fibrosarcomas and osteosarcomas were different from the osteoblast expression patterns. Thus, it became apparent that the osteoblast cell cultures of the invention are pure cultures not rendered impure by other cell types.

The osteoporosis diagnosing method of the invention is based on the determination of suitable osteoblast-specific differentiation markers permitting statements concerning the early differentiation phase of the osteoblasts, the biosynthesis and maturation of the extracellular matrix, and the late osteoblast differentiation phase.

It was found that the cell proliferation rate and expression of at least six osteoblast-specific differentiation markers should be determined quantitatively, and in addition to the cell proliferation rate, at least one parameter of the early differentiation phase of the osteoblasts, at least one parameter of the late differentiation phase, and at least four parameters of the matrix synthesis should be determined in order to obtain an at least 95% reliable statement.

Preferably, in examining the early differentiation phase, the expression of one of the three oncogenes c-myc, c-fos or c-jun, particularly c-fos, is determined in addition to the cell proliferation rate, the expression of intracellular alkaline phosphatase, collagen type I and type IV and chondroitin sulfate or hyaluronic acid in examining the formation and maturation of the extracellular matrix, and the intracellular synthesis of osteocalcin in examining the late differentiation phase.

The expression intensities of these parameters are compared to those of primary osteoblast cell cultures from non-osteoporotic test persons of same sex and about same age and subjected to statistical assessment, e.g., by means of a discriminant analysis. Of course, additional differentiation markers such as growth factors (e.g., TGF-0), cytokins (e.g., IGF I, IGF II), alkaline phosphatase secreted into the cell supernatant, as well as secreted collagen type I and type IV may be determined in order to augment the reliability of the statements.

In examining the early differentiation phase of the osteoblasts, the cell proliferation rate in parallel cultures is measured after 48–196 hours of incubation, preferably after 72 hours of incubation. Measurement is conducted using common cell proliferation assays, e.g., by incorporating a radiolabelled substance such as $^3$H-thymidine in the DNA. Also, the assay for incorporating bromodeoxyuridine developed by the Boehringer Mannheim GmbH is suitable for determination. It appeared that a 4–6 times reduced cell proliferation capacity is an indication for an osteoporotic patient (cf., FIG. 3).

In addition, the expression of the three oncogenes c-fos, c-myc and c-jun is specific for early differentiation of osteoblasts. Preferably, the expression of c-fos was determined. The expression of oncogenes is determined quantitatively after the same incubation period as in the case of the cell proliferation rate, using immunohistochemical staining of their protein products in the monolayer cell cultures and spectrophotometry.

In addition, a quantification of the steady state level of respectively specific mRNA by quantitative PCR and optionally, a Northern blot analysis (if possible depending on cell number) may be performed in order to examine the early differentiation phase of the osteoblasts.

The cell proliferation rates and the oncogene expression intensities in the osteoporotic and non-osteoporotic cells are compared, and a statement concerning the presence of osteoporosis is made, or these parameters together with those of the late differentiation phase and the matrix synthesis are subjected to statistical evaluation.

When examining the biosynthesis and maturation of the extracellular matrix produced by osteoporotic and non-osteoporotic cells, at least the intracellular alkaline phosphatase, collagen type I and type IV, chondroitin sulfate or hyaluronic acid are determined quantitatively after an incubation period of from 3 to 14 days, preferably after 3 to 7 days, using immunohistochemical staining of their protein products and spectrophotometry. It appeared that osteoblasts from osteoporotic patients express 4-5 times more alkaline phosphatase than osteoblasts from healthy patients (cf., FIG. 4). Likewise, membrane-bound chondroitin sulfate is expressed more strongly by osteoblasts from osteoporotic patients.

The inventive determination of the expression of alkaline phosphatase in osteoblast cell cultures of osteoporotic and non-osteoporotic patients permits statements concerning not only an already manifest but also a beginning osteoporosis. A beginning osteoporosis is characterized by a slight increase in the endogenous expression of alkaline phosphatase, whereas in a manifest osteoporosis, the endogenous expression of alkaline phosphatase is massively increased.

In addition to the above-mentioned parameters, the quantitative determination of growth factors such as TGF-$\beta$, especially TGF-$\beta_2$, and cytokins such as IGF I and IGF II, using immunohistochemical staining of their protein products and spectrophotometry, may also be used in the further examination of formation and maturation of the extracellular matrix.

The determination of the BMP's (bone morphogenetic proteins) in the osteoblastic cells may provide additional information relating to the disease.

In examining the formation and maturation of the extracellular matrix, the respectively specific mRNA may be determined additionally by quantitative PCR and Northern blot.

Optionally, alkaline phosphatase secreted into the cell culture supernatant, as well as collagen type I and IV may be quantified as additional parameters.

To examine the late differentiation phase of the osteoblasts (mineralization process), reagents promoting mineralization are added to the parallel bone cell cultures, and the intracellular synthesis of osteocalcin is determined quantitatively. This determination is preferably performed using immunohistochemical staining and spectrophotometry.

The detection of osteocalcin-specific mRNA may be carried out in addition and is effected using quantitative PCR.

As an additional measure, freshly synthesized mineral matrix and the formation of mineralization nodes may also be detected during the late differentiation phase by staining with silver nitrate according to van Kossa.

Once the 7 parameter mentioned as minimum (cell proliferation, an oncogene, alkaline phosphatase, collagen type I and IV, chondroitin sulfate or hyaluronic acid, osteocalcin) have been determined, evaluation is effected by comparison with those of non-osteoporotic cells and optionally, using statistics, where discriminant analysis has proven particularly useful.

It appeared that the proliferation rate of cells recovered from osteoporotic patients was significantly lower compared to the proliferation rate of healthy patients. Where the c-fos oncogene and TGF-$\beta_2$ expression of cells recovered from osteoporotic patients is significantly lower, and the chondroitin sulfate and osteocalcin expression is higher compared to the expression rate of the respective differentiation markers of cells from non-osteoporotic patients, an osteoporotic disease is present. The alkaline phosphatase synthesis rate in osteoblasts recovered from osteoporotic patients is significantly higher than the alkaline phosphatase expression in osteoblasts of non-osteoporotic patients.

Consequently, the method of the invention allows an up to 95% reliable statement concerning the presence of osteoporosis on the basis of the cell cultures according to the invention by merely determining the above-mentioned 7 parameters which are measured using methods common to a person skilled in the art.

Surprisingly, it appeared that the cell cultures of the invention are also excellently suited for testing potential therapeutic agents for osteoporosis and thus, an in vitro test system is available, permitting examination of the direct effect of potential therapeutic agents on individual human osteoblast precursor cells from healthy test persons and patients.

Therefore, the present invention is also directed to the method for testing potential therapeutic agents for osteoporosis according to claim 7 and claim 8.

It appeared that the mitogenic effect of potential osteoporosis therapeutic agents may also be determined by measuring the cell proliferation rate using common methods as described (cf., FIG. 5).

The effect of potential osteoporosis therapeutic agents on the differentiation of "osteoporotic" osteoblast precursor cells may also be determined by measuring the above-described minimum parameters for the diagnosis of osteoporosis. In this case as well, a reliable statement is obtained by the mere determination of the above-mentioned parameters using immunohistochemical staining and spectrophotometry.

In addition, the effect of potential osteoporosis therapeutic agents on the regulation of the matrix synthesis may be determined via detection of specific mRNA using quantitative PCR. The determination is performed in such a way that the total RNA is isolated from the cells, a cDNA library is prepared from mRNA using oligo and/or random primers and reverse transcriptase, and the determined amount of respectively specific single-stranded cDNA is amplified using specific primer pairs. For quantification, the M-actin fragment is amplified as housekeeping gene in parallel, using PCR.

This test is an excellent supplement for animal models currently used in examining osteoporosis therapeutic agents, which have only limited capability in corresponding to human symptoms and by no means allow for an individual determination of particularly suited therapeutic agents. When sampling bone substances from patients suffering from other skeletal diseases, it is possible to test the effect of potential therapeutic agents against these skeletal diseases as well, using cell cultures established therefrom according to the invention.

The standardized primary osteoblast cell cultures according to the invention obtained from osteoporotic patients can be prepared in reproducible fashion using the above-described method and maintained viable for up to two years. They represent pure cultures which may be identified unequivocally by means of high-resolution 2D SDS gel electrophoresis and can be distinguished from osteoblast cell cultures from non-osteoporotic patients.

The invention is also directed to the use of these primary osteoblast cell cultures in diagnosing osteoporosis and in testing potential osteoporosis therapeutic agents.

With reference to the figures and embodiments which are not intended to be limiting, the invention will be illustrated in more detail below.

DETAILED DESCRIPTION OF THE INVENTION 1. Cell cultivation

The cell culture model is based on primary cell cultures prepared from iliac crest biopsies from patients with suspected osteoporosis characterized using differential diagnosis. The iliac crest biopsies were taken from 26 osteoporotic and 18 non-osteoporotic female patients aged from 50 to 70 years.

All of the punched-out bone samples were treated as follows:

Following washing of the punched-out pieces with PBS and removal of fat and connective tissues possibly present, each of the bone pieces was treated five times with dilute collagenase solution (0.5 mg/ml) by Worthington (CLS 2) at 37° C for 30 minutes. α-MEM medium and HAM-F12 medium by Gibco at a ratio of 1:2 without addition of serum was used to dilute the collagenase solution.

Each of the fractions thus obtained was washed in a medium containing serum (medium as described above), taken up in a medium containing 3% Ultroser and cultivated. 2. Cell culture conditions Over the entire experimental period, the cells were cultivated in a serum-containing medium consisting of equal portions of (α-MEM medium and HAM-F12 medium by Gibco, and the medium was exchanged twice a week.

The cells from fractions 1 to 3 were grown and passed continuously. 3. Determination of the cell Droliferation rate 3,000 osteoblastic cells from fractions t1 to 2 up to the second passage, recovered from osteoporotic patients (OP cells), per well of a 96-well microwell plate were incubated in the presence of 10% FCS and 10% inactivated human control serum in a cell culture medium (α-MEM and HAM-S F12 medium 1:12) for 48 h, 120 h and 192 h. In parallel, 3,000 osteoblastic cells from non-osteoporotic patients were incubated under the same conditions. The number of intact cells was determined by means of trypan blue staining and counting in a counting chamber. 4. Determination of the cell proliferation rate under the influence of the three growth factors 1, 2 and 3 using bromodeoxyuridine incorporation (BrdU incorporation) Growth factor 1 =TGF-$\beta_2$

2 =IGF I

3 =IGF II

Cells from fraction 1 and/or 2 of each punched-out bone piece up to the 2nd passage were used in the proliferation test.

$3 \times 10^3$ cells from the first and/or second passage per well of a 96-well plate and 200 µl of medium were used.

The cells were cultivated for three days under the conditions previously described and subsequently cultivated further for one day in medium with no serum until subconfluence was reached.

Thereafter, the three growth factors 1, 2 and 3 were added to the cells at four different final concentrations (100, 10, 1, and 0.1 ng/ml medium).

Cells in a medium containing 10% FKS and in a medium containing 5% Ultroser served as controls.

Triplets were set up for all concentrations and controls.

Six wells including cells, to which no bromodeoxyuridine had been added during the proliferation test served as blank controls.

After 54 hours of incubation with the growth factors, the proliferation test (5-Bromo-2'-deoxyuridine Labeling and Detection Kit III by Boehringer Mannheim) was initiated by adding 20 µl of labelling solution diluted 1:90 in 1% BSA medium and subsequent incubation for 18 hours.

The proliferation test was conducted according to the manufacturer's instructions.

Evaluation of the proliferation test was effected by measuring the optical density (OD) at 405 nm in an ELISA reader. After 60 minutes of color development, the absorbance was measured 12 times at intervals of 5 minutes.

The values obtained are apparent from Table 1.

In FIG. 5, the measured absorbance of each of the three growth factors is illustrated as a function of the concentration.

TABLE 1

Effect of TGF-$\beta_2$, IGF II and IGF I on human osteoblast precursor cells

| Growth factor | | Absorbance mean value | Standard deviation |
|---|---|---|---|
| TGF-$\beta_2$ | 100 ng/ml | 0.190 | 0.002 |
| | 10 ng/ml | 0.190 | 0.002 |
| | 1 ng/ml | 0.170 | 0.008 |
| | 0.1 ng/ml | 0.150 | 0.004 |
| IGF I | 100 ng/ml | 0.140 | 0.008 |
| | 10 ng/ml | 0.140 | 0.002 |
| | 1 ng/ml | 0.148 | 0.006 |
| | 0.1 ng/ml | 0.151 | 0.005 |
| IGF II | 100 ng/ml | 0.140 | 0.000 |
| | 10 ng/ml | 0.139 | 0.001 |
| | 1 ng/ml | 0.150 | 0.001 |
| | 0.1 ng/ml | 0.148 | 0.004 |
| | 10% FKS | 0.194 | 0.014 |
| | 5% Ultroser | 0.157 | 0.003 |
| | 3% Ultroser | 0.144 | 0.008 |
| | 1% BSA | 0.145 | 0.001 |
| Blank | | 0.131 | 0.001 |

5. Conducting the high-resolution 2D SDS gel electrophoresis (IEF SDS PAGE)

The 2D SDS gel electrophoresis of the NOP and OP cell extracts was conducted as described in "Electrophoresis" 1994, 15, 685–707, p. 686.

First dimension:
  isoelectrical focussing (IEF) (left
  side of gel: acidic proteins with IP, e.g., of 4;
  right side of gel: proteins with IP, e.g., of 8)

Second dimension:
  SDS PAGE under reducing conditions (proteins of lower molecular weight appear in the lower region, those with high molecular weight in the upper region)

The evaluation of the spot intensities was effected using scanning densitometry and statistics. 6. Examination procedures and materials Determination of intracellular and secreted alkaline phosphatase (AP)

Cell culture conditions:

3,000 osteoblastic cells from fractions 1 and 2 up to the second passage, recovered from osteoporotic patients (OP cells), per well of a 96-well microwell plate were preincubated in the presence of 10% FCS and 10% inactivated human control serum in a cell culture medium (α-MEM and HAM-S F12 medium) for 24 h. In parallel, 3,000 osteoblastic cells from non-osteoporotic patients were cultivated under the same conditions.

AP assay:

The cells were cultivated for three days under the conditions described and subsequently, the AP assay was carried out. The cells were washed twice with phosphate buffer by Dulbecco and subsequently lysed each time using 100 µl of a solution consisting of 0.1 M glycine, pH 10.3, 1 mM $ZnCl_2$, 1 mM $MgCl_2$ and 0.1% Triton X-100. To each of the wells of a microwell plate, 50 µl of a 2.5 mM solution of disodium 4-nitrophenyl phosphate hexahydrate (AP reagent) was added, and the development of coloration was measured at 405 nm within one hour at intervals of 15 minutes in a TITERTEK ELISA reader. The enzymatic activity correlates with the color intensity and is expressed as nM p-nitrophenyl phosphate as substrate per cell number determined. In parallel, a dilution series of a 1 mM 4-nitrophenol solution was pipetted as standard. Cells in a medium containing 10% FCS served as controls.

PCR:

Amplification of mRNA coding for osteoblast-specific differentiation markers, using the reverse transcriptase-polymerase chain reaction (RT-PCR)

The amplification of specific mRNA sequences using RT-PCR is carried out by a) isolation of total RNA; b) synthesis of single-stranded cDNA by transcribing mRNA into cDNA using Superscript II reverse transcriptase and oligo-dT or random primer; c) amplification of cDNA fragments specifically coding for the osteoblast differentiation markers, using PCR; d) detection of specifically amplified PCR products on agarose gels.

Isolation of total RNA

The total RNA from 1–2 million osteoblasts and osteoblast-like cells was isolated (Trizol Kit, Gibco Life Technologies).

Synthesis of single-stranded cDNA by transcribing mRNA into cDNA using Superscript II reverse transcriptase and oligo-dT or random primer Up to a half microgram of the total RNA or 5–50 ng of mRNA per sample was transcribed using Superscript II reverse transcriptase and 500 ng of oligo-dT or 500 pg of random primer (Superscript II Reverse Transcriptase Kit, Gibco, Life Technologies) at 420C. for 50 minutes.

The resulting CDNA is used as template for amplification in the PCR.

Amplification of cDNA fragments specifically coding for the osteoblast differentiation markers, using PCR One tenth of the single-stranded cDNA sample (see above) was amplified in 2 mM Tris-HCl; pH 8.4; 5 mM KCl; 1.5 mM $MgCl_2$; 10 mM sense amplification primer, 10 mM anti-sense amplification primer under the following PCR conditions (preferably):

Denaturation: 10 min

Eight PCR cycles were run as follows:
Denaturation at 94° C., 45 s;
Annealing: 58° C., 1 min, 45 s, extension at 72° C., 3 min;

This was followed by 25 PCR cycles:
Denaturation at 94° C., 45 s;
Annealing: 55° C., 45 s; extension at 72° C., 3min;
Extension: 72° C., 10 min.

Gel electrophoresis of PCR products

One tenth to one twentieth part of the PCR product was separated on 0.7%–1.2% agarose gel for a half hour at 60 V constant voltage, and the molecular weights of amplified PCR products were compared with a DNA marker.

Sense and antisense primer sequences

The primer pair sequences specific for cDNA coding for osteoblast differentiation markers were selected by the co.don GmbH with the aid of MacMolly Tetra Software (Prof. B. Wittig).

Northern Blotting

Detection of osteoblast differentiation marker-specific mRNA:

The detection of specific mRNA sequences by hybridization is effected by separating the total RNA on an agarose gel matrix, transferring and subsequently fixing same on a filter and hybridizing with a specific DNA probe.

Isolation of total RNA

The total RNA from 10–20 million osteoblasts and osteoblast-like cells was isolated (Trizol Kit by Gibco).

RNA gel electrophoresis

From five to ten micrograms of each total RNA were separated on a 1.2% formaldehyde agarose gel for one hour at a constant voltage of 100 V.

Transfer

Following electrophoresis, the gels were placed on an amphoteric Nytran membrane (Schleicher & Schuell) for one hour, blotted overnight and subsequently, the nucleic acids were crosslinked using UV radiation.

Labelling the DNA probe

Each time, a cDNA fragment 40 bases in length and specific for the osteoblast differentiation markers to be examined was amplified using the polymerase chain reaction (PCR) and subsequently incubated with biotin reagent Bio-ULS (Dianova GmbH) for one hour at 87° C.

Hybridization

Following UV crosslinking, the nitrocellulose membrane was pre-hybridized with 0.1 mg/ml herring sperm DNA in 75 mM sodium citrate puffer, 750 mM NaCl, 5% polyvinylpyrrolidone, 0.1% BSA, 5 mM EDTA, 0.5% SDS at 42° C. for 15 minutes and then incubated for 16 hours at 42° C. in a solution of 50% formamide, 1% bovine serum albumin, 1 mM EDTA, 0.5 mM sodium phosphate, 5% sodium dodecyl sulfate, and specific biotin-labeled DNA probe (about 100 ng).

Detection of mRNA

Following hybridization, the membrane was washed, blocked with 1.5% dry milk solution, and incubated in a solution of streptavidin/alkaline phosphatase (Schleicher & Schuell) solution for from 15 minutes to 3 hours. Thereafter, the membrane was washed with 0.5% Tween-20, PBS solution for 5 minutes and the color formation was effected by incubating the membrane in 0.1 M Tris-HCl; 0.1 M NaCl; 5 mg $MgCl_2$, NBT (32 mg/ml) in 70% dimethylformamide, BCIP (16 mg/ml) for 1–16 hours.

Primer/DNA probe sequences

The sequences of the primer pairs and/or DNA hybridization probes, which represent cDNA specifically coding for osteoblast differentiation markers, were selected using MacMolly Tetra Software (Prof. B. Witting).

Performing the immunohistochemical staining

Principle: Detection of cellular antigens in a confluent cell rug using a specific antibody through a second antibody (enzyme or biotin conjugate) and subsequent detection by substrate cleavage Cells were seeded at a concentration of from $1 \times 10^3$ to $5 \times 10^4$ cells/well and incubated in an incubator at 37° C until a confluent cell rug had formed The medium is sucked off and washed 3 times with PBS Cell fixation: add 100 µl of ice-cold methanol/well, incubate at 4° C. for 10 to 20 min, wash with PBS 3 times Saturating free binding sites in the well: add 100 µl of 2% skimmed milk to PBS/well, agitate at room temperature (RT) for 1 h or at 4° C. overnight; beat out or suck off plate Add 50 µl of respective specific antibody and agitate at RT for 1 h or at 4° C. overnight; wash 3 times with PBS Add 50 µl of 2nd antibody (peroxidase conjugate; the specific goat-anti-rabbit or goat-anti-mouse anti-bodies by Sigma were used) and agitate at RT for 1 h or at 4° C. overnight; wash 5 times with PBS Addition of substrate: 100 µl (soluble, ABTS) of substrate solution (ABTS=2,2'-azinobis(3-ethylbenzthiazoline-6-sulfonic acid) dissolve tablet in 100 ml of 0.05 M phosphate-citrate buffer, pH 5.0 (25.7 ml of disodium hydrogen phosphate+ 24.3 ml of citric acid) and 25 µl of 30% hydrogen peroxide, distilled water to make 100 ml; incubate in the dark for 60 minutes Add 100 µl of substrate to well A12 (background); measure optical density (OD) at 405 nm in the ELISA reader Specific antibodies used:

| | |
|---|---|
| for hyaluronic acid: | mouse-anti-hyaluronate MAb (CamonSerotec # MCA 277) |
| for chondroitin sulfate: | mouse-anti-chondroin sulfate MAb (Sigma # C 8035) |
| for collagen type I: | mouse-anti-human collagen Type I MAb (Chemicon # MAK 8035) |
| for collagen type IV: | mouse-anti-human collagen type IV MAb (Sigma # 1926) |
| for TGF-β: | mouse-anti-TGF-β-1,2,3 MAb (Sigma # B 3026) |
| for c-fos: | rabbit-anti-c-fos AB, polyclonal (Dianova # PC 05) |
| for c-jun: | rabbit-anti-c-fjun AB, polyclonal (Dianova # PC 07) |
| for c-myc: | mouse-anti-c-myc MAb (Dianova # OP 10) |
| for osteocalcin: | rabbit-anti-human osteocalcin Ab (Paesel+Lorei # 14-143-0071) |

7. Statistical evaluation using discriminant analysis

Using discriminant analysis, an osteoblast cell culture is assigned to the group of patients suffering from osteoporosis or the group of healthy individuals as a result of the cellular proliferation rate and the expression intensities of cellular differentiation markers.

It is the aim to determine those coefficients with best possible resolution of the discriminant function values.

Considering the 7 tested variables according to the invention, the discriminant analysis of osteoblastic cells from patients suffering from osteoporosis and those who do not provides the following data:

| | |
|---|---|
| Correct group assignment: | 95.1% |
| Discriminant analysis coefficient: | 0.8217 |
| Significance p of discriminant: | 90.0000 |
| Eigenvalue: | 2.0792 |

It is apparent from the data that NOP and OP are excellently classified.

TABLE 2

Classification table of the discriminant analysis

| Group | Number of samples | Assigned to OP | Assigned to NOP |
|---|---|---|---|
| Osteoporotic cells | 25 | 24 (96.0%) | 1 (4.0%) |
| Non-osteoporotic cells | 16 | 1 (6.2%) | 15 (93.8%) |

The eigenvalue which represents the ratio of the sum of squares between the groups and the sum of squares within the groups is exceedingly high. High eigenvalues indicate good discriminant functions. The results of the discriminant analysis are shown in FIG. 6.

What is claimed is:

1. A method for identifying putative therapeutic agents that may be useful for the treatemnt of osteoporosis which comprises determining the mitogenic effect of the putative therapeutic agents and/or their effect on the differentiation of osteoblast precursor cells in standardized, pure primary cultures from osteoporotic patients prepared by sequential enztmatic digestion of transiliacal bone biopsies and cultivation osteoblast precursor cells, analyzing effects of the putative therapeutic agents on the following parameters with the osteoplast precursor cells from osteoporotic patients
   a) expression of intracellular proteins as determined on a high-resolution two dimensional sodium dodecyl sulfate polyacrylamide gel electrophoresis;
   b) a quantitative determination of the cell proliferation rate; and
   c) a determination of expression of at least six osteoblast-specific differentiation markers including,
      i) expression of c-myc, c-fos or c-jun as a parameter of the early differentiation phase of the osteoblasts,
      ii) intracellular synthesis of osteocalcin as a parameter of the late differentiation phase and,
      iii) expression of intracellular alkaline phosphatase, collagen type I, collagen type IV and chondroitin sulfate or hyaluronic acid as parameter of matrix synthesis;

wherein said osteoblast precursor cells are cultured in a cell culture medium, which consists essentially of α-MEM medium and HAM-F12 medium in a ratio of 1:3 to 3:1 and optionally serum in a concentration of 1–12%; and comparing the effects to the same parameters analyzed with the osteoplast precursor cells in the absence of the putative therapeutic agents.

2. The method according to claim 1, wherein in examining the early differentiation phase of the osteoblasts, the expression of c_fos is determined in b), in addition to the cell proliferation rate.

3. The method of claim 1, wherein the sequential enzymatic digestion is performed using collegegenase.

* * * * *